(12) United States Patent
Prinzel, III et al.

(10) Patent No.: US 9,283,468 B2
(45) Date of Patent: Mar. 15, 2016

(54) METHOD AND APPARATUS FOR PERFORMANCE OPTIMIZATION THROUGH PHYSICAL PERTURBATION OF TASK ELEMENTS

(71) Applicant: The United States of America as represented by the Administrator of the National Aeronautics and Space Administration, Washington, DC (US)

(72) Inventors: Lawrence J. Prinzel, III, Newport News, VA (US); Alan T. Pope, Poquoson, VA (US); Olafur S. Palsson, Durham, NC (US); Marsha J. Turner, Chapel Hill, NC (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 24 days.

(21) Appl. No.: 14/153,434

(22) Filed: Jan. 13, 2014

(65) Prior Publication Data

US 2014/0156039 A1 Jun. 5, 2014

Related U.S. Application Data

(63) Continuation of application No. 11/129,756, filed on May 13, 2005, now Pat. No. 8,628,333.

(60) Provisional application No. 60/610,870, filed on Sep. 10, 2004.

(51) Int. Cl.
*A63B 71/06* (2006.01)
*A61B 5/00* (2006.01)

(Continued)

(52) U.S. Cl.
CPC .............. *A63B 71/06* (2013.01); *A61B 5/0002* (2013.01); *A61B 5/0205* (2013.01); *A61B 5/486* (2013.01); *A63B 69/00* (2013.01); *A63B 69/0024* (2013.01); *A61B 5/021* (2013.01); *A61B 5/024* (2013.01); *A61B 5/0402* (2013.01); *A61B 5/0476* (2013.01); *A61B 5/0531* (2013.01);

(Continued)

(58) Field of Classification Search
CPC ....................................................... A63B 71/06
USPC ............................ 434/236, 247, 252; 700/91
See application file for complete search history.

(56) References Cited

U.S. PATENT DOCUMENTS 5,697,791 A * 12/1997 Nashner et al. ............... 434/247
5,743,744 A    4/1998 Cassily et al.

(Continued)

*Primary Examiner* — Timothy Musselman
*Assistant Examiner* — Alvin Carlos
(74) *Attorney, Agent, or Firm* — Jennifer L. Riley

(57) ABSTRACT

The invention is an apparatus and method of biofeedback training for attaining a physiological state optimally consistent with the successful performance of a task, wherein the probability of successfully completing the task is made is inversely proportional to a physiological difference value, computed as the absolute value of the difference between at least one physiological signal optimally consistent with the successful performance of the task and at least one corresponding measured physiological signal of a trainee performing the task. The probability of successfully completing the task is made inversely proportional to the physiological difference value by making one or more measurable physical attributes of the environment in which the task is performed, and upon which completion of the task depends, vary in inverse proportion to the physiological difference value.

20 Claims, 2 Drawing Sheets

(51) Int. Cl.
*A61B 5/0205* (2006.01)
*A63B 69/00* (2006.01)
*A61B 5/021* (2006.01)
*A61B 5/024* (2006.01)
*A61B 5/0402* (2006.01)
*A61B 5/0476* (2006.01)
*A61B 5/053* (2006.01)
*A61B 5/16* (2006.01)
*A63B 67/02* (2006.01)

(52) U.S. Cl.
CPC ............ *A61B 5/16* (2013.01); *A63B 2067/025* (2013.01); *A63B 2225/50* (2013.01); *A63B 2230/00* (2013.01)

(56) References Cited

U.S. PATENT DOCUMENTS

| | | | |
|---|---|---|---|
| 5,907,819 A * | 5/1999 | Johnson | 702/152 |
| 6,067,468 A | 5/2000 | Korenman et al. | |
| 6,148,280 A * | 11/2000 | Kramer | 702/153 |
| 6,212,427 B1 | 4/2001 | Hoover | |
| 6,259,889 B1 | 7/2001 | LaDue | |
| 6,277,030 B1 | 8/2001 | Baynton et al. | |
| 6,425,764 B1 | 7/2002 | Lamson | |
| 6,463,385 B1 | 10/2002 | Fry | |
| 6,491,647 B1 | 12/2002 | Bridger et al. | |
| 6,527,700 B1 | 3/2003 | Manico et al. | |
| 6,774,885 B1 * | 8/2004 | Even-Zohar | 345/156 |

* cited by examiner

METHOD AND APPARATUS FOR PERFORMANCE OPTIMIZATION THROUGH PHYSICAL PERTURBATION OF TASK ELEMENTS

CROSS-REFERENCE TO RELATED APPLICATIONS

This patent application is a continuation of U.S. patent application Ser. No. 11/129,756, filed on May 13, 2005, which claims the benefit of and priority to U.S. Provisional Patent Application No. 60/610,870, filed on Sep. 10, 2004. Each of the foregoing applications are hereby incorporated by reference in their entirety.

ORIGIN OF THE INVENTION

The invention described herein was made in part by employees of the United States Government and may be manufactured and used by and for the Government of the Untied States for governmental purposes without the payment of any royalties thereon or therefor.

BACKGROUND OF THE INVENTION

1. Technical Field

This invention relates generally to human performance psychology and to an apparatus and method of biofeedback used to improve human performance.

2. Related Art

The human nervous system is responsible for a number of physiological functions that are either vital to life, or to the normal performance of a bodily function, or to the normal performance of organ systems supportive of life. Examples of human physiological functions include mentation, respiration, digestion, circulation, excretion, sight, and hearing.

In general, human physiological functions may be associated with one or more electrical signals (hereinafter "physiological signals") by techniques that are well known in the biomedical arts. Examples of physiological signals include the electrical activity of muscle that is detected, measured and recorded by an electromyogram ("EMG"), and the electrical activity of the heart that is detected, measured and recorded by an electrocardiogram ("ECG"). Other examples of physiological signals include, inter alia, the respiratory rate ("RR"), heart rate ("HR"), blood pressure ("BP"), skin temperature ("ST"), and the galvanic skin response ("GSR").

Measured values of physiological signals may be associated with physiological states and may be used to define the presence of such states. For example, in a physiological state of anxiety, adrenaline diverts blood from the body surface to the core of the body in response to a perceived danger. As warm blood is withdrawn from the surface of the skin, the ST drops. Similarly, in a physiological state of stress, perspiration generally increases making the skin more conductive to the passage of an electrical current, thereby increasing the GSR. In a like manner, the EMG may be used to measure the tension present in certain muscles, thereby serving as an index of the overall tension experienced by a person.

Electrical brainwave activity is another physiological function productive of physiological signals that may also be associated with physiological states. An EEG recording is made by attaching one or more pairs of electrodes to a person's scalp using an electrically conductive gel. Each electrode-pair comprises an EEG channel. Channels are placed on the scalp in a grid-like pattern accordance with a convention. Convention also categorically defines detected brainwave electrical activity according to such features as frequency and amplitude. Brainwave activity changes situationally and with a person's physiological state. Particular mental tasks also alter the pattern of brain waves in different parts of the brain. Formerly output to a galvanometer coupled to an inkpen for tracing brainwave activity across a moving paper strip, modern EEG channels output their signals to digital-to-analog converters for subsequent input into a computer for programmed display.

It is well known in the field of performance psychology that the peak performance of a task, such as, for example, putting in golf, foul shooting in basketball, serving in tennis, marksmanship in archery or on a gunnery range, shooting pool, or throwing darts, requires the presence of a physiological state, comprising one or more optimal measured values of physiological signals, coincident with the physical performance of the task. The presence of such an optimal physiological state in athletics is colloquially referred to as "being in the zone."

An optimal physiological state for the performance of a task is obtained if all of the measured values of physiological signals indicating or defining the physiological state are equal to all of the values which are measured when a defined task is successfully performed with a defined frequency, in a defined number of repetitions, such as, for example, making a foul shot from a foul line 9 times out of 10, or sinking a putt in a single stroke on a golf green 9 times out of 10.

Biofeedback generally refers to an area of physiological research and technology by which a subject is trained to exert conscious control over certain unconscious physiological functions, such as those discussed hereinabove. The measured values of physiological signals of a subject may be received by a biofeedback device as inputs from a variety of biosensing devices and then displayed on an output device of the biofeedback device, i.e., "fed back" to the subject, so that the subject is able to monitor them and to learn to consciously control the physiological signals.

Biofeedback devices use computer programs to enable a person to see his or her own measured values of selected physiological signals through the use of biosensing devices placed on various sites on the person's body. For example, a thermistor may be placed on a person's fingertip for the measurement of ST, or, for example, an EEG electrode may be placed on the person's scalp for outputting brainwave patterns. The measured values of such exemplary physiological signals from such biosensing devices are output to a computer that is programmed to display this information in ways that are useful to the person. Once the measured values of a person's physiological signals are available, i.e., "fed back" to the person, self-regulation of these parameters can be achieved through several methodologies. Physiological self-regulation training has been shown to benefit health as well as performance of athletic and other expert tasks.

The programmed displays of biofeedback information vary. Some programs, for example, cause the display of bars representative of physiological difference values, each computed as the difference between a measured value of a person's physiological signal and a corresponding, predefined desirable physiological value, that is consistent with the optimal performance of a defined task, such as, for example, target shooting, or, the invocation of a defined state, such as, for example, a meditative state. The bars move up and down on the display to reflect the magnitude of the physiological difference value, growing taller as the difference value increases, or growing smaller as the difference value decreases; and, consequently feeding back information relevant to the achievement of certain predefined goals or targets in physiological self-regulation that are optimally consistent with the desired task or achievement of the desired state. Other programs display difference values through the movement or relative location of animated icons or cartoon characters.

Methods used by persons to consciously alter measured values of physiological signals also vary, and for example include such techniques known in the biofeedback arts as diaphragmatic breathing, clearing of the mind, external focusing, creative imagery, progressive relaxation and cognitive restructuring.

Significantly, self-regulation of physiological signals cannot be forced. Rather, it must be encouraged and supported until self-regulatory mastery is accomplished, not unlike learning self-balancing on an upright bicycle as a child. Neither accomplishment can be willed. It can only be grasped or apprehended in a moment of realization achieved through encouragement, support and practice.

Accordingly, in utilizing biofeedback for physiological self-regulation to invoke or attain measured values of desired physiological signals consistent with the optimal performance of a desired task, the values of desired physiological signals are initially set at more attainable target values, which values are altered as proficiency in self-regulation progresses. That is, the desired physiological target values are initially set to make the attainment of the self-regulatory goal easier. Thereafter, the bar is gradually raised in keeping with the self-regulatory proficiency of the person.

Presently, methods of biofeedback used in performance psychology suffer from a number of disaffecting limitations. Initially, prevailing systems and methods of biofeedback training require numerous training sessions involving near-relentless repetition in order to master biofeedback and enjoy its benefits. Often, an athlete or trainee cannot maintain the motivation required to fully realize the performance payoff of biofeedback. Additionally, prevailing systems and methods of biofeedback training are non-contextual, occurring, as they do, at a time (and, usually, place) away from the performance of the action or movement. This requires the athlete or trainee to "hold on" to the practiced mental state until the action or movement is performed.

The present invention overcomes these limitations by:
 [i] providing an apparatus and method of performance-enhancing biofeedback training that has intuitive and motivational appeal to the trainee, by tightly embedding the biofeedback training in the actual task whose performance is to be improved; and,
 [ii] providing an apparatus and method of performance-enhancing biofeedback training that is operational in real-time, precisely at the moment when a task or exercise, such as an athletic or military maneuver, is required to be performed.

No prevailing systems and methods of biofeedback training used in performance psychology simultaneously integrate biofeedback training of the optimal mental state with practice in executing an action or movement.

The present invention makes practicing the optimal mental state and executing the movement both part of the same practice challenge by engineering the two tasks into the same practice device. This difference provides at least three additional advantages:
 [i] The trainee's brain comes to more closely associate the optimal mental state with the look and feel of the performance setting and equipment, as well as the muscle action involved in executing the movement, so that the trainee is better able to later reproduce that state when immersed in the cues of the real situation.
 [ii] Unlike prevailing sport mental training systems and methods, the present invention has intuitive appeal to the trainee by tightly embedding the biofeedback training in the actual task that the trainee wants to perform better. The trainee is required to simultaneously master the muscle skill and the optimal mental state; the trainee is rewarded for mastering the mental state by having the practice environment actually physically change to cooperate with, rather than frustrate, his attempts perform a task.
 [iii] The biofeedback that the trainee observes, and is motivated to control, changes features of the practice environment that actually physically affect the trainee's likelihood of succeeding in the desired performance.

Prevailing mental training systems and methods are not helpful at the moment of execution of performance because they employ distracting displays and sounds that are foreign to the performance setting. Furthermore, these forms of feedback are not as motivating because they do not physically impact success in performance.

The feedback behavior of the physical environment provided by the present invention has the added benefit of providing aids to visualization that the trainee can use in the real-world skill performance setting. The present invention physically actualizes what the relevant art calls on the trainee to imagine.

BRIEF SUMMARY OF THE INVENTION

The present invention is a method and apparatus for training at least one trainee engaged in the performance of a task to attain a physiological state consistent with the optimal performance of said task, comprising a physiological difference value for said task and a capture probability for completing said task, said physiological difference value being computed as the absolute value of the difference between at least one target value and at least one corresponding measured physiological signal of said at least one trainee engaged in the performance of said task, and said capture probability being inversely proportional to said physiological difference value.

DETAILED DESCRIPTION OF THE INVENTION

Figure 1:
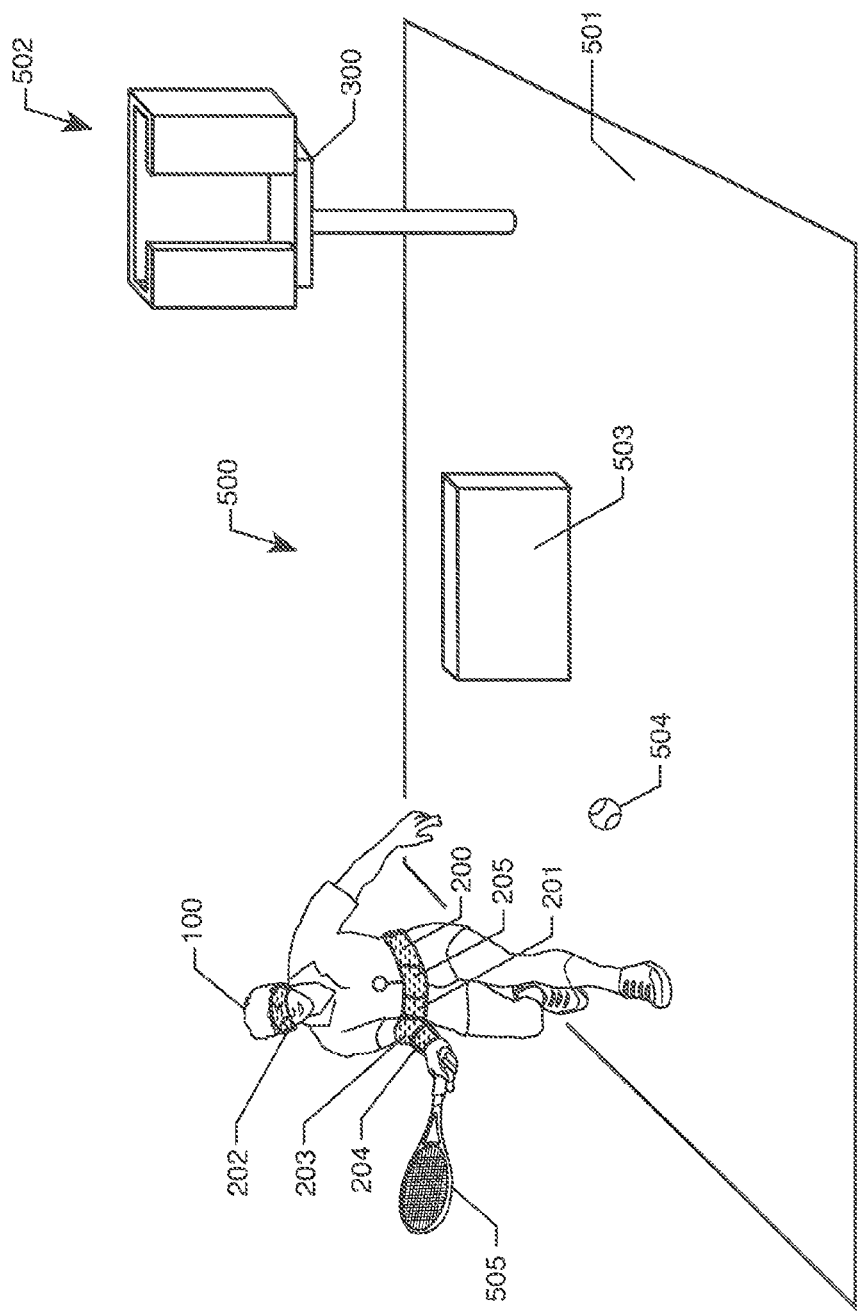
FIG. 1 is a schematic diagram illustrative of inventive elements common to most embodiments of the invention.

As used hereinafter the terms "measured value of a physiological signal" or "measured value" mean the magnitude of a human physiological signal, including central nervous system electroencephalographic activity and muscular electromyographic activity.

As used herein, the term "measured physiological state" refers to the combined state of body and mind of a human being as defined by a set comprising at least one measured value of a physiological signal.

As used herein, the term "target value consistent with the optimal performance of a task" or "target value" refers to a physiological signal that is substantially equal to either the mean, median, or mode of a corresponding measured value of a physiological signal that is present when a defined task is successfully performed with a defined frequency, i.e., a defined number times out of a defined number of attempts, such as, for example, successfully making a foul shout in basketball 9 times out of 10 attempts.

As used herein, the term "physiological state consistent with the optimal performance of a task" or "target physiological state" refers to a physiological state that is present if each of the measured values of the physiological signals comprising the aforesaid set defining a measured physiological state is substantially equal to each of either the mean, median, or mode of the corresponding measured value of a physiological signals that is present when a defined task is successfully performed with a defined frequency, i.e., a defined number times out of a defined number of attempts, such as, for example, successfully making a foul shout in basketball 9 times out of 10 attempts.

As used herein, the term "physiological difference value" or "difference value," means the absolute value of the difference between a target value and a measured value.

The learning and performance of a task by a human being, (hereinafter a "task") such as, for example, the performance of an athletic maneuver, or the execution of military combat exercise, such as, for example, marksmanship training, is both defined and determined by several universal features (hereinafter "task elements").

Generally, a task is performed by a trainee in a:
[i] task environment having a
[ii] task surface, such as, for example, a field, court, lane, alley, range, course, arena, or other two- or three-dimensional physical setting provided with demarcated zones for legitimate and illegitimate maneuvers, such as, for example, serve zones in tennis, or foul zones in basketball, and, within which there are disposed physical objects in the nature of
[iii] moveable or static barriers or obstructions, such as, for example, a net on a tennis court or a sand trap on a golf course, or barbed wire on a military obstacle course. The task is usually accomplished by gloved or bare hands with or without a
[iv] task device, such as, for example, a sporting implement—racket, golf club, bat, or stick, or a weapon—firearm, bow, or other tool, or with one or both hands serving as an task device. The task may involve a
[v] projectile, such as a ball, puck, Frisbee, birdie, dart, arrow, bullet, shell, rocket, or paintball, that is made to course through a trajectory or path by use of the task device, the objective of the task being to place the projectile within, through, over or upon a
[vi] target, such as a goal region in football, hockey or lacrosse, a basketball hoop, a strike zone in baseball, a bullseye, or a defined region, such as that painted on a tennis court for receiving a legitimate serve.

The foregoing task elements—
[i] task environment,
[ii] task surface,
[iii] movable or static obstacles and barriers,
[iv] task device,
[v] projectile, and
[vi] target—each plays a role in determining the probability of whether the goal of the task—hitting the target—is accomplished successfully.

In tasks involving athletic performance, the contribution of several of the foregoing task elements to the probability of successfully accomplishing the goal (hereinafter the "capture probability") is fixed. For example, the dimensions of the task environment, such as a green on a golf course, are fixed. The dimensions and position of the target, such as, for example, the size and location of a golf hole on a green are fixed. The physical attributes of the task device, such as, for example, a golf club, are also fixed while the club is in play. The dimensions of the projectile, such as a golf ball, are likewise fixed. Accordingly, the capture probability in most tasks is essentially determined by the physical skill of the trainee. With the exception of climate, virtually nothing in the environment of the trainee operates to influence the skill brought to bear to accomplish the task.

The present invention departs from convention in order to teach a trainee to invoke or access a physiological state that is consistent with the optimal performance of a designated task. By physically modulating various physical attributes of the foregoing task elements in conjunction with biofeedback technology, trainees are taught to self-regulate selected physiological signals in order attain a predefined or selectable target physiological state consistent with the optimal performance of the designated task.

The invention makes the capture probability depend on more than the physical skill of the trainee, by additionally making the capture probability inversely proportional to a physiological difference value, that is computed as the absolute value of the difference between a predefined or selectable target physiological state and a measured physiological state of the trainee. In effect, the fixed maximum capture probability that obtains in the absence of any modulation of the various physical attributes of the foregoing task elements—the most favorable capture probability—is initially reduced by the modulation of various physical attributes of the foregoing task elements to a less favorable capture probability; and, it is the biofeedback-moderated self-regulatory skill of the trainee that determines the degree to which the capture probability is restored to its fixed maximum value for performing the exercise.

The present invention is an apparatus and method of physiological biofeedback training for practicing the attainment of a physiological state that is consistent with the optimal performance of a task, such as, for example, a military or athletic maneuver, as follows. The invention modulates at least one physical feature of a task element associated with the performance of a task, such as, for example, in the case of putting a golf ball:
[i] modulating the accuracy of a golf club; and/or,
[ii] modulating the stability of the surface of a putting green; and/or,
[iii] modulating the slope of the surface of a putting green; and/or,
[iv] modulating the distance between a golfer and the golf hole; and/or,
[v] modulating the regulation surface area that a golf hole presents to a golf ball.

These task elements are conventionally fixed by rules of an exercise, maneuver or game, such as, in the case of putting a golf ball, the rules promulgated by the Professional Golf Association (PGA). The modulation of the task element has the effect of altering the probability of successfully performing a physical action or maneuver essential to completing the task successfully (hereinafter "capture probability"), such as, for example, successfully sinking a putt with a single stroke in a game of golf.

In the invention, the capture probability—the probability of successfully performing the physical task—is made an inverse function of the extent to which a measured physiological state of the subject performing the task departs from a predefined or selectable physiological state that is consistent with the optimal performance of the task (hereinafter "target physiological state").

The modulation of a task element is accomplished by:

[i] operationally connecting to a trainee at least one biosensing device that is an operative component of a portable biofeedback device, the biosensors of which are attached to a trainee;

[ii] using the biosensing device to measure the trainee's physiological state by measuring at least one physiological signal of the trainee;

[iii] outputting the measurement obtained by the biosensing device as a signal encoding the measured value of the physiological signal to a computing device, that is an operative component of the portable biofeedback device, for comparison to a preprogrammed, wirelessly downloadable, or trainee-input corresponding target value;

[iv] using the computing device to compute a physiological difference value as the absolute value of the difference between the measured value of the physiological signal and the target value of the physiological signal;

[v] using the computing device to display the physiological difference value to the trainee by a display device, that is an operative component of the biofeedback device, using graphical, auditory or tactile or substantially equivalent means of communicating the physiological difference value to the trainee;

[vi] using an encoding device and a transceiver to transmit a physiological difference signal, encoding the physiological difference value, to at least one computer-driven mechanical system that is programmed to alter the task element in a manner that renders the performance of the task increasingly difficult as the physiological difference value increases.

Continuing with the example of sinking a putt in a game of golf, a computer-driven mechanical system, such as a servomechanism, upon receipt of the foregoing physiological difference signal, may, for example, alter the area of the golf hole presented to the golf ball using a variable aperture iris-diaphragm disposed over the golf hole; or, for example, upon receipt of the foregoing physiological difference signal, a computer-driven mechanical system, such as a servomechanism, may be used to increase the length or grade of the putting green between the trainee and the golf hole; or, as a further example, upon receipt of the foregoing difference signal, a computer-driven mechanical system, such as a vibrator motor, may be used to cause the golf club to vibrate in proportional magnitude to the difference signal.

Referring now to the drawings in which like parts are designated by like numerals in the various views, FIG. 1 shows a schematic diagram illustrative of inventive elements common to all embodiments of the invention. In FIG. 1, a trainee 100 stands in a task environment 500 having a task surface 501, upon which there is disposed at least one target 502 and optionally a movable or static task barrier 503.

Trainee 100 utilizes task device 505 to perform the task of propelling a projectile 504 at target 502. Trainee 100 wears a portable biofeedback device 200 operatively connected to at least one portable input device 204 and at least one portable output device 203. Computing device 201 receives as input at least one measured value of a physiological signal of the trainee from at least one biosensing device 202, that is also an operative component of biofeedback device 200, and is operationally connected to trainee 100.

Computing device 201 may, for example, comprise a mobile computing or communications device, such as, for example, a personal digital assistant ("PDA"), hand-held, wrist-worn, or garment-borne communications or computing device, a lightweight notebook computer, a pager, a cellular telephone, or any combination thereof.

Computing device 201 is programmed to compute a physiological difference value as the absolute value of the difference ence a measured value of a physiological signal of trainee 100, and a corresponding target value of the same physiological signal, which target value has either been stored or wirelessly downloaded in computing device 201, or has been selectably input by trainee 100 using an input device 204.

Examples of measured values of physiological signals of trainee 100 output by one or more biosensing devices 202 for which computing device 201 may store corresponding optimal values of physiological signals of trainee 100 include, without limitation, EEG brainwaves, EMG signals, ECG signals ST, BP, HR, GSR and RR.

Computing device 201 is programmed to output measured values, target values and difference values to portable output device 203 for display to trainee 100 in order to enable trainee 100 to modify the physiological difference value by using input device 204 to either increase the target value by any percentage, thereby increasing the physiological difference value, or to either decrease the target value or supplement the measured value by any percentage, thereby reducing the physiological difference value.

Portable output device 203 may, for example, comprise a miniaturized video output device, such as a wrist-borne display screen, display goggles, a spectacle-mounted video output device, a head-mounted video output device, and audio output devices, such as ear phones or headsets worn by a trainee 100. Portable input device 204 may, for example, comprise a miniaturized joystick, an appropriately modified videogame control pad, a miniaturized keyboard, a track pad, a touch-screen, a cellular telephone keypad, or a PDA keypad.

Computing device 201 is programmed to enable trainee 100 to vary ("shape") the target value that determines the magnitude of the physiological self-regulatory change required of trainee 100. Shaping may entail reinforcing successive approximations of a desired response. Alternatively, shaping may be conducted by altering a measured value of a trainee so that the measured value as altered more closely approximates a target value. The alteration may be incrementally removed as a trainee's proficiency in self-regulation progresses. As used herein, shaping is analogous to "spotting" in weight training, wherein a weight-lifting trainee is assisted by having another person support some weight during some lift repetitions, and gradually supporting less weight, as the trainee's strength increases over training sessions. Accordingly, computation of a difference value may be preceded by incrementing or decrementing a target value by a percentage of a previously assigned target value, selected by the trainee, a trainee's assistant or coach, or an algorithm.

Following shaping, the one or more of such physiological difference values that have been displayed to trainee 100 on output device 203 are encoded by an encoding device (not shown in FIG. 2) in a signal and wirelessly transmitted by a trainee transceiver 205 that is an operative component of biofeedback device 200 to at least one computer-controlled mechanical system 300, such as, for example, a computer-controlled servomechanism, that is adapted to receive the physiological difference value that has been encoded in the wirelessly transmitted signal, and to modulate at least one manipulatable physical feature of a task element having a parametric value, so as to make that parametric value inversely proportional to the physiological difference value. In FIG. 1, computer-controlled mechanical system 300 is shown as being operationally connected to target (target task element) 502. The physical feature of target 502 having a parametric value that may be made inversely proportional to the physiological difference value may be the area that target 502 presents to projectile 504.

Figure 2:
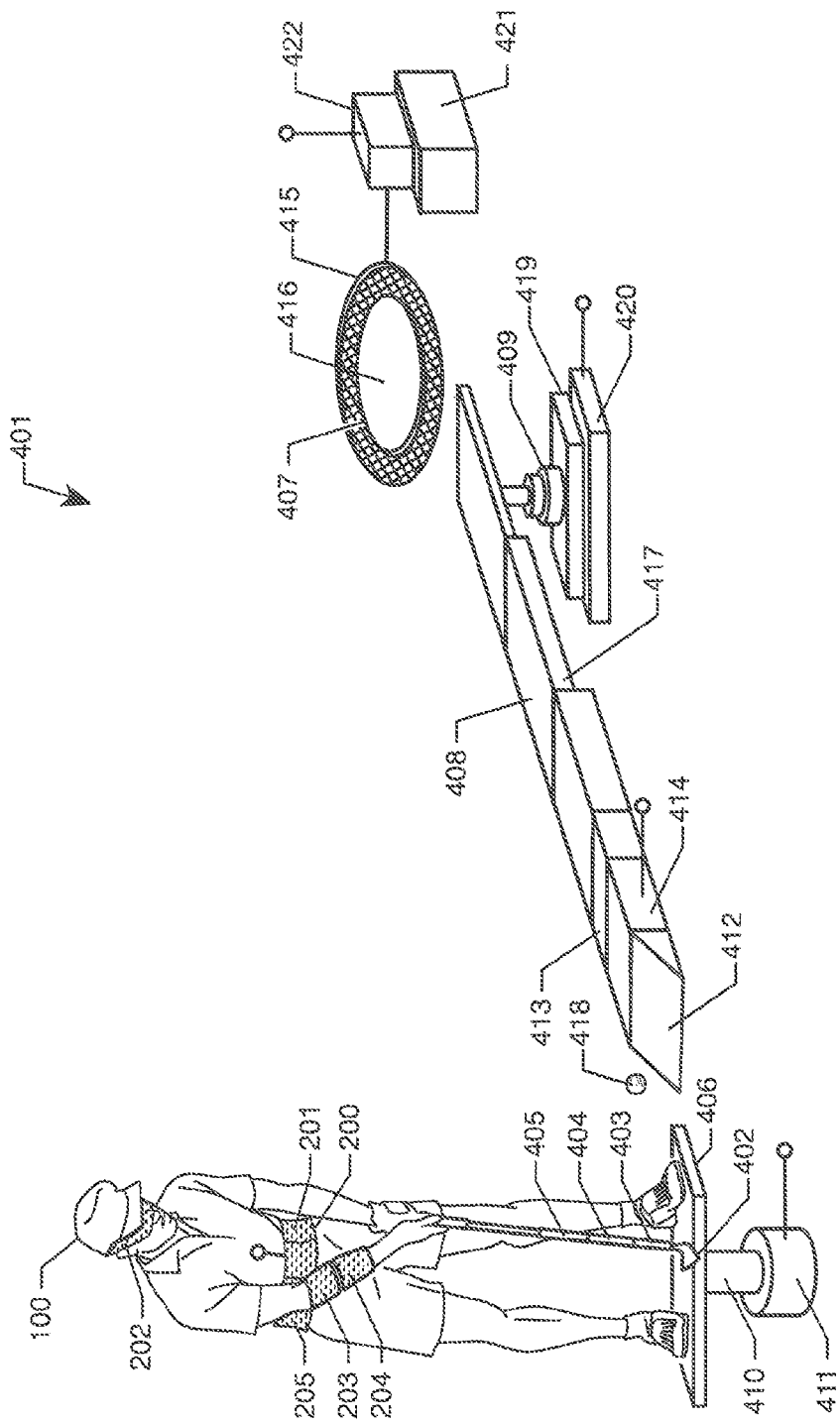
FIG. 2 is a schematic diagram illustrative of a golf-putting embodiment of the invention.

For example, FIG. 2 shows a golf-putting embodiment of the invention, wherein trainee 100 wearing biofeedback device 200 stands in a golf green 401 (task environment element) while engaged in the task of putting a golf ball 418 (projectile task element) into a golf hole (target task element) 407 over a golf path 417 (task environment element) using a golf club 402 (device task element), to do so in a single stroke.

Golf green 401 is adapted to the putting task as follows:

[i] a first vibratory device 403 may be attached to golf club 402 to induce a vibration of a variable frequency and amplitude that is controlled by a first computer-controlled vibratory system 404, equipped with a first vibratory system transceiver 405 that is operationally connected to first vibratory device 403. First computer-controlled vibratory system 404 decreases the reciprocal of the frequency or decreases the reciprocal of the amplitude of the vibration induced in golf club 402 by first vibratory device 403, as a physiological difference value wirelessly transmitted to it by biofeedback device 200 increases, thereby decreasing the accuracy of golf club 402 from its baseline nonvibratory state as the physiological difference value wirelessly transmitted to first vibratory device 403 by biofeedback device 200 increases, consequently making the task of putting more difficult; and/or

[ii] a second vibratory device 406 may be operationally disposed upon surface 408 of golf path 417 lying between trainee 100 and golf hole 407, to induce vibration or undulation of surface 408 of golf path 417 lying between trainee 100 and golf hole 407, which vibration or undulation has a variable frequency and amplitude that is controlled by a second computer-controlled vibratory system 410, equipped with a second vibratory system transceiver 411 that is operationally connected to second vibratory device 406. Second computer-controlled vibratory system 410 decreases the reciprocal of the frequency of vibration or undulation, or decreases the reciprocal of the amplitude of vibration or undulation induced upon surface 408 or a portion thereof, by second vibratory device 406, as the physiological difference value wirelessly transmitted to it by biofeedback device 200 increases, thereby decreasing the accuracy of the path followed by putted golf ball 418 to golf hole 407 from its baseline nonvibratory state as the physiological difference value wirelessly transmitted to second vibratory device 406 increases, consequently making the task of putting more difficult; and/or

[iii] an elevating device 409 may be operationally attached beneath surface 408 of golf path 417 lying between trainee 100 and golf hole 407 to alter its baseline zero surface gradient using a computer-controlled elevating system 419 equipped with an elevating device transceiver 420 that is operationally connected to elevating device 409. Computer-controlled elevating system 419 decreases the reciprocal of the surface gradient of surface 408 as the physiological difference value wirelessly transmitted to elevating device 409 by biofeedback device 200 increases, thereby elevating the surface 408 of golf path 417 and making the task more difficult; and/or,

[iv] a telescoping surface displacement device 412 may be operationally inserted onto surface 408 of golf path 417 lying between trainee 100 and golf hole 407, to extend the distance between trainee 100 and golf hole 407, which distance extension is controlled by a computer-controlled displacement system 413, equipped with a displacement system transceiver 414, and operationally connected to telescoping surface displacement device 412. Computer-controlled displacement system 412 decreases the reciprocal of the distance between trainee 100 and golf hole 407 as the physiological difference value wirelessly transmitted to it by biofeedback device 200 increases, and causes the distance between trainee 100 and golf hole 407 to increase, consequently making the task of putting more difficult; and/or

[v] a variable aperture iris diaphragm device 415 may be disposed over golf hole 407 to alter the baseline circular area presented by the surface opening 416 of golf hole 407 to golf ball 418 using a computer-controlled aperture system 421 equipped with an aperture system transceiver 422 that is operationally connected to variable aperture iris diaphragm device 415. Computer-controlled aperture system 421 decreases the circular area presented by surface opening 416 of golf hole 407, as the physiological difference value wirelessly transmitted to it by biofeedback device 200 increases, thereby making the task of putting more difficult.

Additionally, some tasks may be divided into subtasks performed over a sequence subintervals of the time during which an overall task is performed. The performance of these subtasks during these subintervals cumulatively contributes to performance of the overall task. Continuing with the example of sinking a putt in a game of golf, this overall task may be broken down into:

[i] a first subtask of lining up the golf putt prior to approaching the ball, performed during a first subinterval;

[ii] a second subtask of approaching the ball, performed during a second subinterval; and,

[iii] a third subtask of standing over the ball in an effective posture prior to the putting stroke, performed in a third subinterval.

The target value of a physiological signal may differ among these subintervals. For example, a target value associated with focus and concentration, such as a high beta brainwave EEG signal and a low theta brainwave EEG signal could be operative for the subtask of lining up the golf putt prior to approaching the ball; a target value associated with low autonomic arousal, such as a low skin conductance, or a low heart rate, or a low level of muscle tension reflected in an EMG signal could be operative for the second subtask of approaching the ball; and, a target value associated with a meditative state, such as a high alpha brainwave activity EEG signal could be operative for the third subtask of standing over the ball in an effective posture prior to the putting stroke.

A physiological difference value may also be defined for a particular subinterval and subtask is defined as the absolute value of the difference between a measured value of a physiological signal and the corresponding target value of the physiological signal for that particular subinterval. The modulation by which the task environment responds to the physiological difference value may be programmed to provide biofeedback appropriate to the particular subtask. For example, the opacity of a variable density filter, worn by a trainee, through which the trainee views a putting green, may be made to vary according to a physiological difference value reflecting the focus and concentration the trainee brings to bear to the first subtask of lining up a golf putt prior to approaching the ball. For the second subtask of approaching the ball, the height of a circular barrier around the ball may be made to vary with physiological difference value reflecting the trainee's degree of autonomic arousal. For the third subtask of standing over the ball in an effective posture prior to the putting stroke, features of the task environment may be modulated as described hereinabove.

In all of the foregoing sub-embodiments [a] through [e] inclusive of the golf putting embodiment of the invention, the
  [i] accuracy of the task device (i.e., the golf club);
  [ii] stability of the surface of the task environment (i.e., the putting green);
  [iii] the reciprocal of the surface gradient of the surface of the task environment (i.e., the putting green);
  [iv] the reciprocal of the distance from the trainee to the target (i.e., the length of the putting green); and,
  [v] the area of the target has effectively been made into functions of the physiological difference value that are inversely proportional to the physiological difference value. Accordingly, any increase in the physiological difference value has the effect of decreasing each of these functions, which, taken individually, or taken as any product of two or more of such functions, contribute to decreasing the capture probability, and necessarily rendering the capture probability inversely proportional to the physiological difference value.

Generalizing from the golf putting embodiment, the invention effectively makes the capture probability inversely proportional to the physiological difference value by making the capture probability an approximate parametric function of any one of the following parameters or the product of any two or more of the following parameters:
  [i] the accuracy of the task device;
  [ii] the stability of the surface of the task environment;
  [iii] the reciprocal gradient of the surface of the task environment;
  [iv] the reciprocal distance from the trainee to the target; and,
  [v] the area presented by the target to the projectile, all of which have been made inversely proportional to the physiological difference value by the invention.

Symbolically, if $\alpha$ denotes approximate proportionality, and PDV represents the physiological difference value, then:

$$P_{capture} \alpha 1/(PDV), \quad (1)$$

or $$P_{capture} \alpha P_{capture}[(Accuracy(PDV) \times Stability(PDV) \times 1/Gradient(PDV) \times 1/Distance(PDV) \times Area(PDV)] \quad (2)$$

In equation (1), $P_{capture}$ is a capture probability that is inversely proportional to a physiological difference value PDV; and, in equation (2), $P_{capture}$ is equivalently represented as an approximate parametric function that is the product of an accuracy, a stability, a reciprocal gradient, a reciprocal distance and an area, each of which are inversely proportional to a physiological difference value PDV, to wit:

$$Accuracy(PDV) \alpha 1/(PDV) \quad (3)$$

$$Stability(PDV) \alpha 1/(PDV) \quad (4)$$

$$1/Gradient(PDV) \alpha 1/(PDV) \quad (5)$$

$$1/Distance(PDV) \alpha 1/(PDV) \quad (6)$$

$$Area(PDV) \alpha 1/(PDV) \quad (7)$$

Accordingly, in the foregoing example, trainee 100 employs biofeedback moderated physiological self-regulation to control and adjust his or her physiological state to meet a desired physiological state that it is optimally consistent with the task of sinking the putt in one stroke. Trainee 100 receives immediate feedback regarding his measured physiological state not only through output device 203 of portable biofeedback device 200, but through the invention's physical perturbation of:
  [i] the accuracy of the golf club 402;
  [ii] the stability of putting surface 408;
  [iii] the gradient of putting surface 408;
  [iv] the distance to golf hole 407; and,
  [v] the area 416 of golf hole 407, any one of which, or combination of which, continuously adjust to reflect the extent to which the measured value of the physiological state of trainee 100 departs from a desired physiological state that is optimally consistent with sinking the putt in one stroke.

The objective of the exemplary golf-putting embodiment of the invention is for trainee 100 to move his or her measured physiological signals to values that are increasingly equal to corresponding desired values of physiological functions that are optimally consistent with sinking the putt in one stroke.

The exemplary golf-putting embodiment of the invention rewards successful physiological self-regulation by:
  [i] decreasing vibratory interference with the accuracy of the golf club 402; and/or
  [ii] decreasing vibratory or undulating interference with the stability of putting surface 408; and/or
  [iii] decreasing the gradient of putting surface 408 toward its zero-value baseline; and/or,
  [iv] decreasing the distance to golf hole 407 to its pre-alteration baseline; and/or,
  [v] increasing the area 416 of golf hole 407 to restore it to its baseline area; and/or
  [vi] altering the size, location or motion of a barrier disposed between a trainee and golf hole 407.

The exemplary golf-putting embodiment of the invention is representative of an apparatus for attaining a physiological state consistent with the optimal performance of a task comprising a physiological difference value that is assigned to the task, which physiological difference value is computed as the absolute value of the difference between at least one target physiological function for performing the task and at least one corresponding measured physiological signal of a trainee performing the task, wherein the probability of completing the task by the trainee is inversely proportional to the physiological difference value.

Generalizing from the exemplary golf-putting embodiment, to a generalized embodiment, the generalized embodiment of the invention comprises a task performed in a task environment by at least one trainee operatively connected to a biofeedback device and using a task device having variable accuracy to hit a target with a projectile. The biofeedback device is adapted to wirelessly transmit the physiological difference value. The task environment has a surface with a variable gradient and a variable stability. The target has a variable area, and the target is positioned within the task environment at a variable distance from the trainee.

In the generalized embodiment of the invention, the variable accuracy of the task device is made inversely proportional to the physiological difference value by means of a computer-controlled mechanical system adapted to impart a vibration or undulation to the task device, which vibration or undulation has a reciprocal frequency and a reciprocal amplitude that decrease as the trainee's physiological difference value increases; and, the physiological difference value is received by the computer-controlled mechanical system in the form of an encoded signal that is wirelessly transmitted to it by the biofeedback device.

In the generalized embodiment of the invention, the variable stability of the surface of the task environment is made proportional to the physiological difference value by means of a computer-controlled mechanical system adapted to impart a vibration to the surface of the task environment, which vibration has a reciprocal frequency and a reciprocal amplitude that decrease as the trainee's physiological difference value increases; and, the physiological difference value is received by the computer-controlled mechanical system in the form of an encoded signal that is wirelessly transmitted to it by the biofeedback device.

In the generalized embodiment of the invention, a reciprocal of the variable gradient of the surface of the task environment is made inversely proportional to the physiological difference value by means of a computer-controlled mechanical system adapted to decrease the reciprocal of the variable gradient as the trainee's physiological difference value increases, which physiological difference value is received by the computer-controlled mechanical system in the form of an encoded signal that is wirelessly transmitted to it by the biofeedback device.

In the generalized embodiment of the invention, the variable area of the target is made inversely proportional to the physiological difference value by a computer-controlled mechanical system adapted to decrease the variable area as the trainee's physiological difference value increases, which physiological difference value is received by the computer-controlled mechanical system in the form of an encoded signal that is wirelessly transmitted to it by the biofeedback device.

In the generalized embodiment of the invention, a reciprocal of the variable distance from the trainee to the target is made inversely proportional to the physiological difference by means of a computer-controlled mechanical system adapted to decrease the reciprocal of the variable distance as the trainee's physiological difference value difference increases, which physiological difference value is received by the computer-controlled mechanical system in the form of an encoded signal that is wirelessly transmitted to it by the biofeedback device.

The generalized embodiment of the present invention thus serves as a template for the application of the foregoing enumerated operative principles of the invention in a variety of athletic and military embodiments of which the following examples are representative.

The invention may be practiced such that the task of the invention is successfully serving a tennis ball, in which case:
[i] the task environment would be a tennis court or a portion thereof; and,
[ii] the task device would be a tennis racket; and,
[iii] the projectile would be a tennis ball; and,
[iv] the target would be the demarcated serve zone on the tennis court; and,
[v] the gradient and stability of the surface of the tennis court as well as the distance of the trainee from the demarcated serve zone would remain invariant; and
[vi] the area of the demarcated serve zone on the tennis court would be made inversely proportional to the physiological difference value of the trainee in accordance with the mechanisms of the invention described hereinabove.

The invention may be practiced such that the task of the invention is successfully making a goal in hockey, in which case:
[i] the task environment would be a hockey rink or a portion thereof; and,
[ii] the task device would be a hockey stick; and,
[iii] the projectile would be a hockey puck; and,
[iv] the target would be a hockey goal; and,
[v] the gradient and stability of the surface of the hockey rink would remain invariant; and,
[vi] the distance from the trainee to the hockey goal could be determined, for example, by programmed instructions from the biofeedback device of the invention advising the trainee to skate toward or away from the hockey goal to a new position [at a distance] that would be inversely proportional to the physiological difference value of the trainee; and,
[vii] the area of the hockey goal presented to the hockey puck would be made inversely proportional to the physiological difference value of the trainee in accordance with the mechanisms of the invention described hereinabove, for example, by the use of a two-door shutter device sliding laterally across the area of the hockey goal presented to the hockey puck, having a first door of the shutter that projects medially to the center of the goal from one side of the goal and having a second opposing door of the shutter that projects medially to the center of the goal from the opposing side of the goal, to leave open an area accessible to the hockey puck that is made inversely proportional to the physiological difference value of the trainee.

The invention may be practiced such that the task of the invention is successfully making a goal in lacrosse, in which case:
[i] the task environment would be a lacrosse field or a portion thereof; and,
[ii] the task device would be a lacrosse stick; and,
[iii] the projectile would be a lacrosse ball; and,
[iv] the target would be a lacrosse goal; and,
[v] the gradient and stability of the surface of the lacrosse field would remain invariant; and,
[vi] the distance from the trainee to the lacrosse goal could be determined by programmed instructions from the biofeedback device of the invention advising the trainee to move toward or away from the lacrosse goal to a new position [at a distance] that would be inversely proportional to the physiological difference value of the trainee; and
[vii] the area of the lacrosse goal presented to the lacrosse ball would be made inversely proportional to the physiological difference value of the trainee in accordance with the mechanisms of the invention described hereinabove, for example, by the use of a two-door shutter device sliding laterally across the area of the lacrosse goal presented to lacrosse ball, having a first door of the shutter that projects medially to the center of the goal from one side of the goal and having a second opposing door of the shutter that projects medially to the center of the goal from the opposing side of the goal, to leave open an area accessible to the lacrosse ball that is made inversely proportional to the physiological difference value of the trainee.

The invention may be practiced such that the task of the invention is successfully making a foul shot in basketball, in which case:
[i] the task environment would be a basketball court or a portion thereof; and,
[ii] the task device would be a at least one human hand; and,
[iii] the projectile would be a basketball; and,
[iv] the target would be a basketball hoop; and,
[v] the gradient and stability of the surface of the basketball court would remain invariant; and,

[vi] the distance from the trainee to the basketball hoop would remain invariant; and,

[vii] the area of the basketball hoop presented to the basketball would be made inversely proportional to the physiological difference value of the trainee in accordance with the mechanisms of the invention described hereinabove, for example, by disposing a variable-aperture iris diaphragm over the basketball hoop.

The invention may be practiced such that the task of the invention is successfully kicking a field goal in football, in which case:

[i] the task environment would be a football field or a portion thereof; and,

[ii] the task device would be football footwear; and,

[iii] the projectile would be a football; and,

[iv] the target would be a football goal; and,

[v] the gradient and stability of the surface of the football field would remain invariant; and,

[vi] the distance from the trainee to the football goal could be determined by programmed instructions from the biofeedback device of the invention advising the trainee to move toward or away from the football goal to a new position [at a distance] that would be inversely proportional to the physiological difference value of the trainee; and,

[vii] the area of the football goal presented to the football would be made inversely proportional to the physiological difference value of the trainee in accordance with the mechanisms of the invention described hereinabove, for example, by the use of a two-door shutter device sliding laterally across the area of the football goal presented to football, having a first door of the shutter that projects medially to the center of the goal from one side of the goal, and having a second opposing door of the shutter that projects medially to the center of the goal from the opposing side of the goal, to leave open an area accessible to the football that is made inversely proportional to the physiological difference value of the trainee.

The invention may be practiced such that the task of the invention is successfully pitching a strike in baseball, in which case:

[i] the task environment would be a baseball field or a portion thereof; and,

[ii] the task device would be a pitcher's hand; and,

[iii] the projectile would be a baseball; and,

[iv] the target would be a strike zone; and,

[v] the gradient and stability of the surface of the baseball field would remain invariant; and,

[vi] the distance from the trainee to the strike zone would remain invariant; and,

[vii] the area of the strike zone would be made inversely proportional to the physiological difference value of the trainee in accordance with the mechanisms of the invention described hereinabove, for example, by the use of a two-door shutter device sliding laterally across a mechanical frame encompassing a predefined or regulation strike zone, the mechanical frame also supporting a first door of the shutter projecting medially to the center of the strike zone from one side of the frame, and supporting a second opposing door of the shutter projecting medially to the center of the strike zone from the opposing side of the frame, to leave open an area accessible to the baseball that is made inversely proportional to the physiological difference value of the trainee.

The invention may be practiced such that the task of the invention is using a bow to hit an archery target with an arrow, in which case:

[i] the task environment would be an archery range or a portion thereof; and,

[ii] the task device would be a bow; and,

[iii] the projectile would be an arrow; and,

[iv] the target would be a archery target; and,

[v] the gradient and stability of the archery range or a portion thereof would remain invariant; and,

[vi] the distance from the trainee to the archery target would be made proportional to the physiological difference value of the trainee in accordance with the mechanisms invention described hereinabove, for example, by mounting the archery target on a cord or wire operationally connected to a motorized winch or pulley system that would increase or decrease the distance from the trainee to the archery target to an extent that is inversely proportional to the physiological difference value of the trainee; and

[vii] the area of the archery target would be made inversely proportional to the physiological difference value of the trainee in accordance with the mechanisms of the invention described hereinabove.

The archery embodiment of the invention is easily transposable to such tasks as throwing darts at a bullseye, Olympic javelin throwing or Olympic discus throwing, and military training tasks, such as throwing grenades or grappling hooks.

The invention may be practiced such that the task of the invention is hitting a target with a firearm, in which case:

[i] the task environment would be an firearm range or a portion thereof; and,

[ii] the task device would be a firearm having a variable accuracy, for example, in the form of a gunsight or other mechanical or optical sighting device or that is defocused, disrupted or distorted in accordance with the mechanisms of the invention described hereinabove to an extent that is inversely proportional to the physiological difference value of the trainee, by means of a computer controlled mechanical system adapted to decrease the accuracy of the sighting device as the trainee's physiological difference value increases, which physiological difference value is received by the computer-controlled mechanical system as an encoded signal that is wirelessly transmitted to it by the biofeedback device; and,

[iii] the projectile would be an bullet; and,

[iv] the target would be a firearm target; and,

[v] the gradient and stability of the firearm range or a portion thereof would remain invariant; and,

[vi] the distance from the trainee to the firearm target would be made proportional to the physiological difference value of the trainee in accordance with the mechanisms invention described hereinabove, for example, by mounting the firearm target on a cord or wire operationally connected to a motorized winch or pulley system that would increase or decrease the distance from the trainee to the firearm target to an extent that is inversely proportional to the physiological difference value of the trainee; and

[vii] the area of the firearm target would be made inversely proportional to the physiological difference value of the trainee in accordance with the mechanisms of the invention described hereinabove, for example, by mechanically substituting firearm targets having areas that are inversely proportional to the physiological difference value of the trainee.

The firearms embodiment of the invention is easily transposable to such tasks as paintball marksmanship or military exercises using rocket launchers, antitank weapons and the like.

What is claimed as new and desired to be secured by Letters Patent of the United States is:

1. An apparatus for training at least one trainee engaged in the performance of a task to encourage self-regulation of a physiological state consistent with the optimal performance of said task, comprising:
   a task environment within which said task is being performed, said environment having a surface with a variable gradient and a variable stability;
   a movable barrier of variable area moving at a variable speed;
   a target having a variable area, said target being positioned within said environment at a variable distance from said at least one trainee;
   a projectile;
   a task device operated by said trainee to attempt to hit said target with said projectile, said task device having a variable accuracy to hit said target with said projectile;
   a biofeedback device operatively connected to said at least one trainee, said biofeedback device adapted to transmit at least one measured physiological signal value of said at least one trainee engaged in the performance of said task, said at least one measured physiological signal value measuring said trainee's current physiological state;
   a computing device configured for computing a physiological difference value for said task, said physiological difference value being computed as the absolute value of the difference between at least one preselected physiological target value and the said at least one corresponding measured physiological signal value of said at least one trainee engaged in the performance of said task; and
   at least one computer-controlled mechanical system configured for altering a capture probability for completing said task by altering at least one of said task environment, said task device, said biofeedback device, said projectile, said target, said barrier, and any combinations thereof, and wherein said capture probability being modified to be inversely proportional to said physiological difference value.

2. The apparatus of claim 1, wherein said variable accuracy of said task device is inversely proportional to said physiological difference value.

3. The apparatus of claim 1, wherein said variable gradient of said surface is proportional to said physiological difference value.

4. The apparatus of claim 1, wherein said variable stability of said surface is inversely proportional to said physiological difference value.

5. The apparatus of claim 1, wherein said variable speed of said movable barrier is proportional to said physiological difference value.

6. The apparatus of claim 1, wherein said variable area of said movable barrier is proportional to said physiological difference value.

7. The apparatus of claim 1, wherein said task device is a golf club and wherein said variable accuracy of said trainee-controlled task device comprises a vibration imparted to said golf club.

8. The apparatus of claim 1, wherein said task comprises putting, said task environment comprises a putting green, said task device comprises a golf club, said projectile comprises a golf ball, said target comprises a golf hole, said variable accuracy of said trainee-controlled task device comprises a vibration imparted to said golf club, said variable gradient of said surface of said putting green has a value of zero, said variable stability of said surface of said putting green is invariant, said variable area of said target comprises an area corresponding to an opening of said golf hole, and said variable distance comprises a distance measured from said trainee to said golf hole, said variable speed of said movable barrier comprises an object of variable speed repeatedly crossing said task environment, and said variable area of said obstruction comprises a barrier of variable cross-sectional area presented to said golf ball.

9. The apparatus of claim 1, wherein said task comprises hitting a target with a firearm, said task environment comprises a firearm firing range, said task device comprises a firearm, said projectile comprises a bullet, said target comprises a firearm target, said variable accuracy of trainee-controlled task device comprises a vibration imparted to said firearm, said variable gradient of said surface of said firearm firing range has a value of zero, said variable stability of said surface of said firearm firing range is invariant, said variable area of said target comprises an area of said firearm target, and said variable distance comprises a distance measured from said trainee to said firearm target.

10. The apparatus of claim 9, wherein said firearm has a variable accuracy sighting device that is made inversely proportional to said physiological difference value by means of a computer controlled mechanical apparatus adapted to decrease said variable accuracy of said sighting device as said difference value increases, said physiological difference value being received by said computer-controlled mechanical apparatus as encoded in a signal that is transmitted to said computer-controlled mechanical apparatus by said biofeedback device.

11. A method for encouraging self-regulation of a physiological state consistent with the optimal performance of a task comprising the steps of:
   a. positioning a trainee within a task environment having a surface;
   b. positioning a target, having a variable area for the receipt of a projectile, within said task environment at a distance from said trainee;
   c. equipping said trainee with a biofeedback device that is worn by said trainee;
   d. equipping said trainee with a task device with which to cast said projectile at said target;
   e. connecting said trainee to at least one biosensing device that is an operative component of said biofeedback device worn by said trainee;
   f. using said biosensing device to measure said trainee's physiological state by measuring at least one physiological signal of said trainee;
   g. outputting said measurement of said trainee's physiological state obtained by said biosensing device as a signal encoding said at least one measured value of said physiological signal to a computing device;
   h. using said computing device to compare said measured value of said physiological signal output to said computing device by said biosensing device to a preprogrammed, or downloaded, or trainee-input corresponding value of a physiological signal that is optimally consistent with the successful performance of said task by said trainee, termed a physiological target value;
   i. using said computing device to compute a physiological difference value as the absolute value of a difference between said measured value of said physiological signal and said corresponding value of a physiological signal that is optimally consistent with said successful performance of said task by said trainee;

j. displaying said physiological difference value to said trainee by means of an auditory or tactile display device that is an operative component of said biofeedback device;

k. using said computing device to transmit said physiological difference value as an encoded signal to at least one computer-controlled mechanical system;

l. providing said task environment with a surface operationally connected to a first computer-controlled mechanical system adapted to impart a vibration or undulation to said surface, said vibration or undulation having a frequency or an amplitude, or both, that increase as said physiological difference value increases, said physiological difference value being received by said computer-controlled mechanical system as encoded in a signal that is transmitted to said computer-controlled mechanical system by said computing device;

m. providing said task environment with a surface operationally connected to a second computer-controlled mechanical system adapted to vary a gradient of said surface in proportion to said physiological difference value by means of a computer-controlled mechanical system adapted to increase said gradient as said physiological difference value increases, said physiological difference value being received by said computer-controlled mechanical system as encoded in a signal that is transmitted to said computer-controlled mechanical system by said computing device;

n. providing said target with a third computer-controlled mechanical system adapted to decrease said variable area as said physiological difference value increases, said physiological difference value being received by said computer-controlled mechanical system as encoded in a signal that is transmitted to said computer-controlled mechanical system by said computing device;

o. providing said task device used by said trainee to cast said projectile at said target with a fourth computer-controlled mechanical system adapted to impart a vibration or undulation to said task device, said vibration or undulation having a frequency or an amplitude, or both, that increase as said physiological difference value increases, said physiological difference value being received by said computer-controlled mechanical system as encoded in a signal that is transmitted to said computer-controlled mechanical system by said computing device;

p. making said distance from said trainee to said target proportional to said physiological difference value by means of a fifth computer-controlled mechanical system adapted to increase said distance as said physiological difference value increases, said physiological difference value being received by said computer-controlled mechanical system as encoded in a signal that is transmitted to said computer-controlled mechanical system by said computing device.

12. The method of claim 11, wherein said task comprises a task performed in said task environment by said at least one trainee operatively connected to said biofeedback device and using said task device having variable accuracy to hit said target with said projectile, said biofeedback device being adapted to transmit said physiological difference value, said task environment having said surface with a variable gradient and a variable stability upon which a task barrier may be disposed, said target having said variable area, and said target being positioned within said environment at a variable distance from said at least one trainee.

13. The method of claim 12, wherein said step of computing said physiological difference value occurs at a time coincident with a time of impact of said task device with said projectile.

14. The method of claim 12, wherein said step of computing said physiological difference value occurs at a time coincident with a time at which said projectile is released to said trainee for hitting said target using said task device.

15. The method of claim 12, wherein said step of computing said physiological difference value is preceded by a step of incrementing or decrementing said physiological target value by a percentage of a previously assigned physiological target value, said percentage being selectable by a said trainee, an assistant to said trainee, or an algorithm.

16. The method of claim 12, wherein said step of displaying comprises displaying and monitoring said measured value, said physiological target value and said physiological difference value to said trainee on a display device having auditory or tactile means for communicating at least one of said measured physiological signal; said physiological target value; and said physiological difference.

17. The method of claim 12, further comprising the steps of:

q. assigning a capture probability to said task; and r. modulating said at least one task element in a manner that decreases said capture probability as said physiological difference value increases, wherein said task element comprises at least one of said vibration to said surface, said variable accuracy of said task device used by said trainee to perform said task, said variable stability of said task surface, said variable gradient of said task surface, said variable area of said target, said vibration of said task device, said variable distance from said trainee to said target, a variable area of said task barrier, a variable speed of said movable barrier.

18. The method of claim 17, wherein said step of modulating said at least one task element begins at a time coincident with said step of computing said physiological difference value and ends at a time coincident with the completion of said task by said trainee.

19. The method of claim 17, wherein said step of modulating said at least one task element begins at a time coincident with said step of computing said physiological difference value and ends at a time determined by said trainee or an assistant to said trainee.

20. The method of claim 17, wherein said step of modulating said at least one task element begins at a time coincident with said step of computing said physiological difference value and ends at a time determined by an algorithm.

* * * * *